(12) United States Patent
Rosenhan

(10) Patent No.: US 11,826,525 B2
(45) Date of Patent: Nov. 28, 2023

(54) CATHETER SECUREMENT DEVICE AND RELATED METHODS

(71) Applicant: SimplicityMD Solutions, LLC, Bountiful, UT (US)

(72) Inventor: Branden D. Rosenhan, Salt Lake City, UT (US)

( * ) Notice: Subject to any disclaimer, the term of this patent is extended or adjusted under 35 U.S.C. 154(b) by 91 days.

(21) Appl. No.: 17/528,077

(22) Filed: Nov. 16, 2021

(65) Prior Publication Data

US 2022/0072277 A1   Mar. 10, 2022

Related U.S. Application Data

(63) Continuation of application No. 16/133,417, filed on Sep. 17, 2018, now abandoned, which is a continuation of application No. 15/350,306, filed on Nov. 14, 2016, now abandoned, which is a continuation of application No. 14/537,902, filed on Nov. 10, 2014, now Pat. No. 9,492,640, said application No. 16/133,417 is a continuation of application No. 14/077,202, filed on Nov. 11, 2013, now abandoned, which is a continuation of application No. 61/902,224, filed on Nov. 9, 2013, and a continuation-in-part of application No. PCT/US2012/036963, filed on May 8, 2012.

(60) Provisional application No. 62/001,629, filed on May 21, 2014, provisional application No. 61/484,117, filed on May 9, 2011.

(51) Int. Cl.
    *A61M 25/02*   (2006.01)

(52) U.S. Cl.
    CPC ....... *A61M 25/02* (2013.01); *A61M 2025/024* (2013.01); *A61M 2025/0246* (2013.01); *A61M 2025/0286* (2013.01)

(58) Field of Classification Search
    CPC .......... A61M 25/02; A61M 2025/0286; A61M 2025/024; A61M 2025/0246
    See application file for complete search history.

(56) References Cited

U.S. PATENT DOCUMENTS

| 4,128,173 A | 12/1978 | Lazarus et al. |
| 4,633,863 A | 1/1987 | Filips |
| 4,645,492 A | 2/1987 | Weeks |
| 4,917,112 A | 4/1990 | Kalt |
| 5,026,352 A | 6/1991 | Anderson |

(Continued)

FOREIGN PATENT DOCUMENTS

| WO | WO/02/061318 | 8/2002 |
| WO | WO/02/061318 A1 | 8/2002 |
| WO | WO/03/035160 | 5/2003 |

OTHER PUBLICATIONS

International PCT Search Report of PCT/US2012/036963 dated Aug. 17, 2012.

(Continued)

*Primary Examiner* — Bradley J Osinski
(74) *Attorney, Agent, or Firm* — Laurence B. Bond

(57) ABSTRACT

A catheter securement device includes a body having a generally curved channel configured to receive a central venous catheter and reposition it in a different direction than the direction of the catheter as it exits the skin of the patient. The securement device includes a cover that slidably connects to the securement device body to prevent the catheter from being pulled out of the curved channel.

13 Claims, 3 Drawing Sheets

(56) References Cited

U.S. PATENT DOCUMENTS

| | | | |
|---|---|---|---|
| 5,167,240 | A | 12/1992 | Rozier et al. |
| 5,226,892 | A | 7/1993 | Boswell |
| 5,690,616 | A | 11/1997 | Mogg |
| 5,713,869 | A | 2/1998 | Morejon |
| 5,766,151 | A | 6/1998 | Valley et al. |
| 5,885,254 | A | 3/1999 | Matyas |
| 5,916,199 | A * | 6/1999 | Miles .................... A61M 25/02 604/174 |
| 6,001,081 | A | 12/1999 | Collen |
| 7,311,697 | B2 | 12/2007 | Osborne |
| 7,709,694 | B2 | 5/2010 | Batich |
| 8,269,058 | B2 | 9/2012 | McCarthy |
| 8,277,417 | B2 | 10/2012 | Fedinec |
| 8,640,738 | B2 | 2/2014 | Zia |
| 8,834,426 | B2 | 9/2014 | Shipman |
| 8,911,396 | B2 | 12/2014 | Gordon |
| 9,492,640 | B2 | 11/2016 | Rosenhan |
| 2005/0047268 | A1 | 3/2005 | Chen |
| 2010/0174240 | A1 | 7/2010 | Wells |
| 2014/0128813 | A1 | 5/2014 | Rosenhan |
| 2015/0133891 | A1 | 5/2015 | Rosenhan |

OTHER PUBLICATIONS

International PCT Examination Report of PCT/US2012/036963 dated Nov. 12, 2013.
Extended EPO Serach Report of EP 2707065 dated Aug. 19, 2014.

* cited by examiner

CATHETER SECUREMENT DEVICE AND RELATED METHODS

CROSS REFERENCE TO RELATED APPLICATIONS

This present application is a continuation of U.S. patent application Ser. No. 16/133,417 filed Sep. 17, 2018 (the "'417 Application"). The '417 application is a continuation of U.S. patent application Ser. No. 15/350,306, filed Nov. 14, 2016 (the "'306 Application"). The '306 application is a continuation of U.S. patent application Ser. No. 14/537,902, filed Nov. 10, 2014 (the "'902 Application"), issued as U.S. Pat. No. 9,492,640 on Nov. 15, 2016. The '902 Application claims the benefit of U.S. Provisional Patent Application Nos. 62/001,629, filed May 21, 2014 and 61/902,224, filed Nov. 9, 2013. This present application is also a continuation of U.S. patent application Ser. No. 14/077,202, filed Nov. 11, 2013 (the "'202 Application"). The '202 Application is a continuation-in-part of PCT/US2012/036963, filed May 8, 2012, which is a non-provisional application and claims the benefit of and priority to U.S. Provisional Patent Application No. 61/484,117, filed May 9, 2011. All of the afore-mentioned applications are hereby incorporated herein in their respective entireties by this reference.

BACKGROUND

A central line catheter ("central venous catheter", "CVC", "central venous line" or "central venous access catheter") or midline catheter (a venous catheter placed in similar locations, but not terminating in a central vein) are catheters placed into a large vein in the neck (internal jugular vein or external jugular vein), chest (subclavian vein) or groin (femoral vein). Central and midline venous catheters are typically used to administer medication or fluids, obtain blood tests (specifically the mixed venous oxygen saturation"), and directly obtain cardiovascular measurements such as the central venous pressure. As used herein the term "catheter" may also refer to a tube designed to drain fluid or material within the abdomen, pelvis, chest or other body cavities, such as are use in pulmonology, critical care, general surgery, orthopedic surgery, interventional radiology and other such specialties where catheters are placed with the primary intent to drain material and not infuse material.

In cases of long term infusion or the long term placement of testing equipment, it is typically necessary for the catheter to remain in place for many days. In order to secure such a central line catheter in position at the injection site, the IV tubing is commonly mounted on a thin flexible pad or seat that is sutured to the patient's skin. This combination of tubing and pad comprises a connector to which one or more other IV supply lines having compatible connectors can be attached.

An example of such an anchor is shown in FIGS. 1-3 labeled generally 2. The anchor 2 has a tubular body 4 and a pair of opposed wings 6. Body 4 has a central channel 8. Central channel 8 is typically sized to be the same diameter as the outer diameter of a catheter 14 (e.g., a multi-lumen catheter having multiple access ports) that is to be secured by the anchor 2. Body 4 often has a longitudinal slit 10 that extends entirely through body 4 along the entire length of body 4. The longitudinal slit 10 is typically placed in the body 4 to allow the anchor to be slipped over the catheter 14 after the catheter 14 is installed in the patient's body (e.g., in the external jugular vein).

The wings 6 of the anchor 2 each have an eyelet 12. In use, a catheter 14 is placed through slit 10 into channel 8. Because of the tight tolerance in the diameter of central channel 8 and the outer diameter of catheter 14, it is very difficult if not impossible to thread catheter 14 through channel 8. Thereafter, anchor 2 is moved to the desired position. Wings 6 are pinched together toward slit 10. A suture 16 is placed through eyelets 12 and tissue into the patient's tissue (not shown) to secure the catheter 14 and the anchor 2 to the patient's tissue.

When the central line catheter is positioned in the jugular vein using the anchor 2 described above, the internal end of the catheter enters the neck of the patient and the external end exits the neck and extends toward the patient's head. A number of problems, however, have arisen with respect to such placement. For example, the location of the access ports can be uncomfortable for the patient and inconvenient for medical personnel to access. In addition, the access ports can extend into the patient's hair and ear, which is a potential route for contamination or infection of the central line. If the patient is of shorter stature, more of the catheter will protrude out of the body and securing the catheter may require suturing or stapling at an inconvenient site very near to or directly under the patient's upper neck, jaw, or ear. Additionally, this current method does little to address the potential for infection at the site where the catheter is inserted under the skin.

BRIEF DESCRIPTION OF THE DRAWINGS

To further clarify the above and other advantages and features of the present disclosure, a more particular description of the embodiments of the invention will be rendered by reference to specific embodiments thereof which are illustrated in the appended drawings. It is appreciated that these drawings depict only illustrated embodiments of the invention and are therefore not to be considered limiting of its scope. The embodiments of the invention will be described and explained with additional specificity and detail through the use of the accompanying drawings in which.

DESCRIPTION

The present disclosure relates to catheter securement devices that have a channel for creating a curve (i.e., bend) in a catheter without causing kinking. For example, the securement device may have a generally curved channel extends from a first end to a second end and is configured for receiving a portion of a catheter to secure the catheter to a patient's body. The securement device may be used to secure a catheter that has an end inserted into a vessel of a patient's body (e.g., a central line catheter, such as a multi-lumen central line catheter). The catheter body causes the catheter to adopt a bent profile that redirects the free end of the catheter away from the direction of catheter exiting the skin, which, for example, reduces the likelihood that the catheter will be accidentally pulled out or dislodged if the free end of the catheter is pulled on. Likewise, the curved channel of the catheter securement device supports the bent profile to greatly reduce risk of kinking the catheter.

The devices of the invention can be used with central line catheters. Central line catheter is installed at an interior jugular location, the catheter securement device allows the free end of the catheter to safely hang down away from the patient's hair and ear for greater patient comfort, ease of access by medical personnel, and reduced danger of infection. Such positioning will also be advantageous to patients, allowing them to freely move without discomfort or limitation. Likewise, when laying in a hospital bed the likelihood of patients rolling over onto the catheter ports when turning will be greatly reduced.

In another embodiment, the present invention relates to a method for securing a central line catheter to a patient's skin. The method includes (1) positioning a catheter in a body lumen or a body cavity of a patient, (2) positioning a free end of the catheter in a catheter securement device as described herein, and (3) securing the catheter securement device to the patient's skin.

In yet another embodiment, a kit is described. The kit may include but is not limited to, a catheter, apparatus for inserting the catheter into a body lumen or a body cavity of a patient, and a catheter securement device as described herein.

Figure 1:
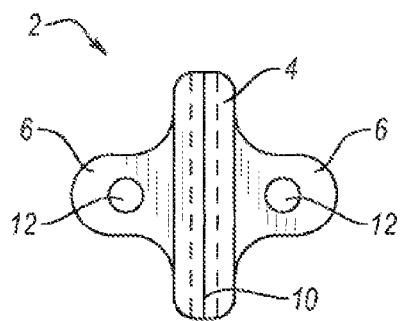
FIG. 1 illustrates a top view of a prior art catheter securement device.
Figure 2:
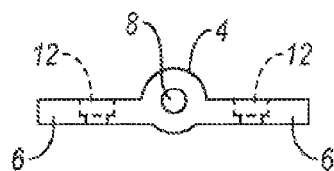
FIG. 2 illustrates an end on view of the catheter securement device of FIG. 1.
Figure 3:
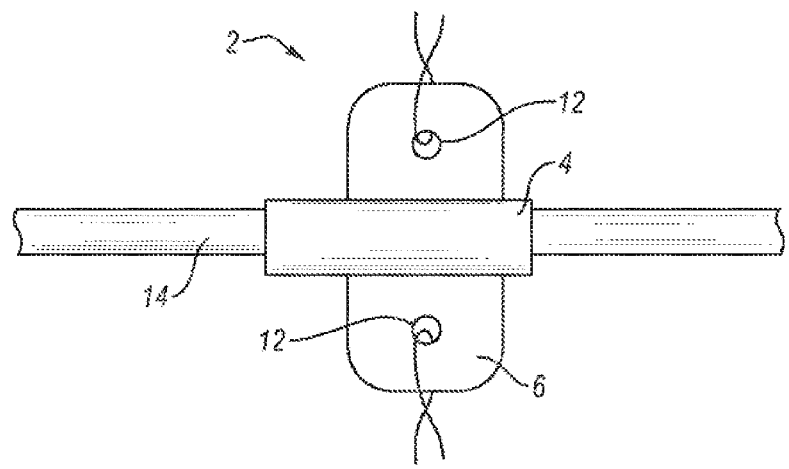
FIG. 3 illustrates the catheter securement device of FIG. 1 in use with a catheter.
Figure 4:
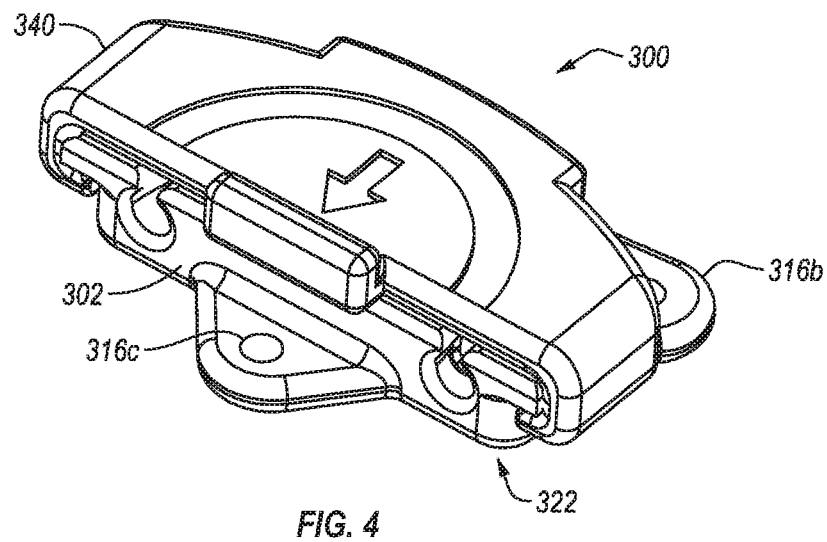
FIG. 4 is a perspective view of a catheter securement device according to one embodiment.
Figure 5:
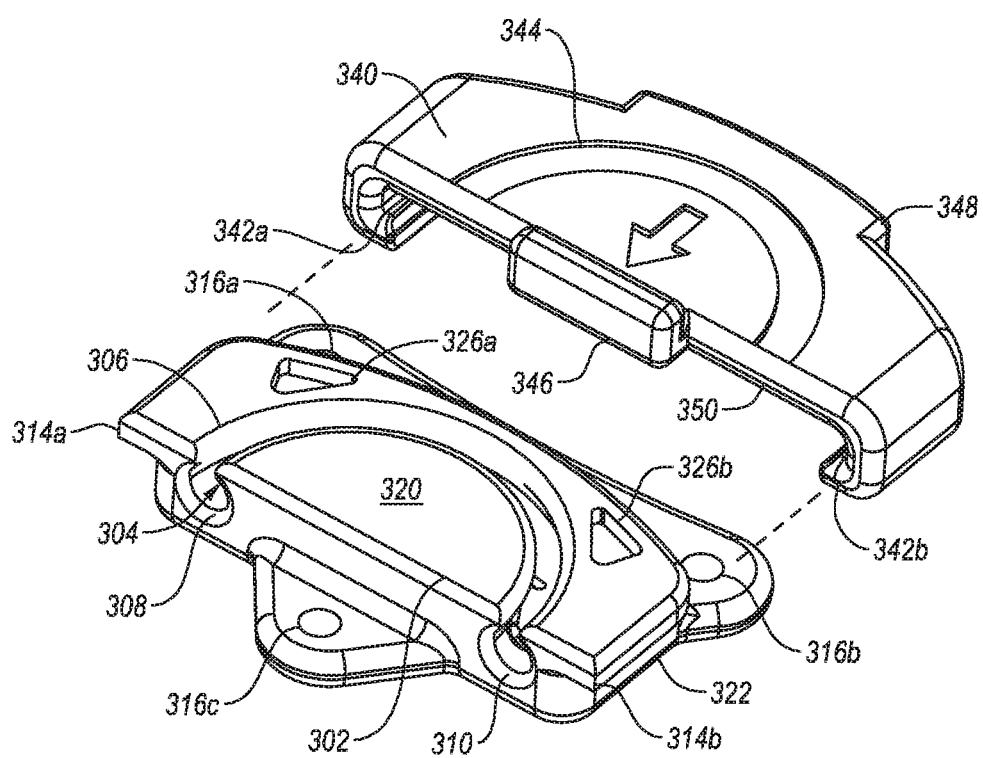
FIG. 5 is an exploded view of the catheter securement device of FIG. 4.
Figure 6:
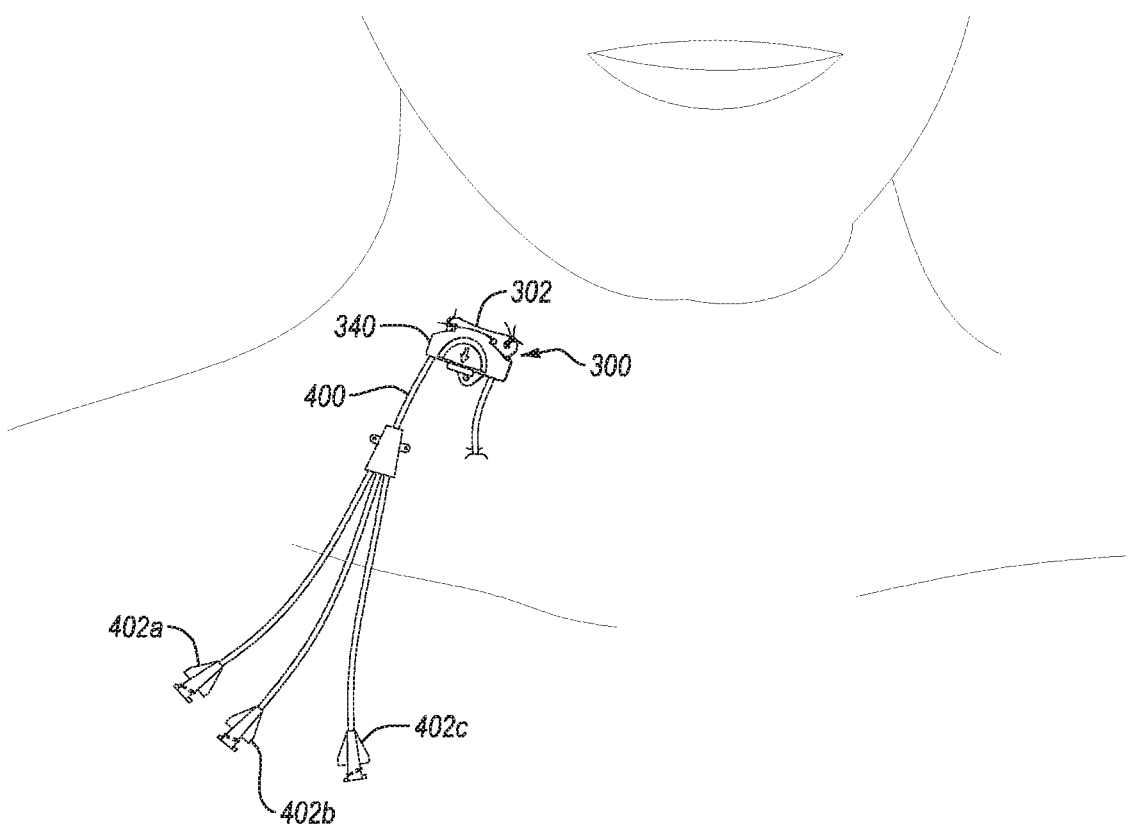
FIG. 6 illustrates the use of the catheter securement device of FIG. 4 on a patient with a central venous catheter placed in the internal jugular vein.

FIGS. 4-6 illustrate an embodiment of a catheter securement device 300 that has a body 302 that releasably couples with a cover 340. Body 302 has a top surface 320 that is opposite a bottom surface 322 that faces the surface of a patient during use (i.e., the skin surface). Body 302 defines a channel 304 having an opening 306 (e.g., a top opening that is parallel to the surface of the patient of a skin when the device is affixed to the skin). Channel 304 and its opening 306 extend from first end 308 to second end 310 and are sized and configured to receive a portion of the tubing of a catheter. Eyelets 318a, 318b, and 318c provide an attachment site for sutures to be looped through the securement device and into a person's skin for attaching the device to the skin.

Cover 340 and body 302 are configured to slidably engage one another. Cover 340 when engaged with body 302 prevents a catheter from exiting channel 304 when the free end of the catheter is pulled. In one embodiment, cover 340 slidably engages body 302 transverse to opening 306. By engaging in the transverse direction, a force in the parallel direction does not cause the cover to disengage. As shown in FIG. 5, body 302 may include extensions 314a and 314b extend laterally on body 302 to form undercuts. Extensions 314 are configured to slidably engage flanges 342a and 342b of cover 340. Cover 340 slides onto body 340 from the side opposite the side where the catheter exits such that the loose ends of the catheter do not interfere with placement of the cover. Cover 340 can include a translucent or transparent portion that allows the catheter to be viewed when cover 340 is in place. For example, cover 340 includes a translucent arc 344. Cover 340 can also include protrusions 346 and 348 that provide a surface for engaging cover 340 to apply and/or remove cover 340 from body 302. In one embodiment, protrusion 346 may extend upward, but flush with edge 350 to avoid interfering with eyelet 316c.

Base 302 may include indentions 326a and 326b that form a bump lock with cover 340. Cover 340 may have protrusions on its underside to engage the indentations. When cover 340 is coupled with body 302 as shown in FIG. 4, indentions 326a and 326b engage cover 304 and prevent it from sliding back off without appropriate force by a user.

The following describes general features that can be used in the foregoing and similar catheter securement devices according to various embodiments of the invention.

In one embodiment, the securement device may define a curved channel with a radius of about 1.5 to about 3 cm, but may be as long as 5 cm to accommodate larger catheters. However, it will be understood that the curved channel can be larger or smaller depending on the diameter of the catheter to be affixed to the body. For example, the curved channel and the channel formed therein can be configured to accommodate a catheter having a size greater than 2, 3, 4, 5, or 6 French and/or less than 20, 15, 12, 8, or 6 French, or within a range of any of the foregoing sizes. For example, the channel may accommodate and grip a channel in a range from about 5 French to about 15 French, or about 7 French to about 9 French. In another example, the channel can be sized with an inner radius of curvature sized to accommodate a catheter having a size in a range from about 5 French to about 7 French and an outer radius of curvature sized to accommodate a catheter having a size in a range from about 9 French to about 11 French. In yet another example, the curved channel includes a pliable material in the channel configured to accommodate and retain catheters having sizes ranging from about 5 French to about 15 French.

In one embodiment, the curved channel bends the catheter at an angle in a range between about 90° and about 210°, or any angle therebetween. For example, the curved channel may define an angle of about 90°, 95°, 100°, 105°, 110°, 115°, 120°, 125°, 130°, 135°, 140°, 145°, 150°, 155°, 160°, 165°, 170°, 175°, 180°, 185°, 190°, 195°, 200°, 205°, or 210° of any range of angles between the forgoing angles. Preferably, the curved channel defines an angle of about 135° or 180°.

Examples of catheters that can be used in the present invention include catheters that have a first end, and a second end, where a portion of the catheter at the second end extends under a patient's skin and into a blood vessel. The first end includes a number of ports (e.g., 1, 2, or 3 ports) in fluid communication with separate lumens in the catheter tubing. The ports can include Luer lock hubs or other mechanisms for attaching a syringe or another device for injection or withdrawal of substances through a selected lumen of the catheter. Likewise, one or all of the hubs can be sealed when they are not being used to prevent blood or fluid loss from the patient and/or to prevent infection.

In some embodiments of the invention the hardness of the catheter securement device material may be selected in combination with wall thickness to give the securement device flexibility that provides patient comfort while avoiding kinking of the catheter. The securement device material may have a shore hardness greater than 40 A, 60 A, 80 A, and less than 85 D, 70 D, 50 D or within a range thereof and a wall thickness greater than 10, 25, 40, 60 thousandths, and less than 200, 150, 120, or 100 thousandths of an inch, or within a range thereof. In some embodiments, the body 302 may be softer or more pliable than cover 340. In this embodiment, the body 302 can be flexible to accommodate the catheter and/or the skin of the patient and the cover can provide rigidity. For example, the body 302 may be made from a silicone or urethane and the cover may be made from a more rigid plastic such as ABS or polycarbonate.

In some embodiments, at least a portion of the channel is configured to circumferentially accommodate a particularly sized catheter (i.e., at least a portion of the channel is tube-like). The device may have a channel wall that extends circumferentially around a catheter by at least 160, 170, 180, or preferably at least 181, 185, 190, 200, 205, 210, 220, 240 degrees and/or less than 270, 250, 230, or 210 degrees or within a range thereof (i.e., has an opening that is 360 degrees minus the forgoing values). In some embodiments, at least and/or less than 10%, 30%, 50%, 80%, or 90% of the catheter in the channel is encircled as described herein and/or a range of the foregoing percentages.

In some embodiments opening 306 is less than the diameter of channel 304. The flexibility of the body material may be selected to allow the opening to flex outward to allow the catheter to be inserted. During manufacturing, the flexibility can also facilitate release of the product from a mold (bump mold).

In one embodiment, the channel may be sized to cause better grip. In this embodiment, the curved channel may have a size that is slightly smaller than the catheter. The channel may be at least 5%, 10%, 15%, or 20% smaller than the catheter to be secured and/or less than 30%, 25%, 20%, or 15% or within a range thereof. Preferably, channels that are smaller than the catheter are also made from a flexible material to allow the channel to expand to accommodate the catheter without crushing the catheter, but creating pressure to grip the catheter. Where the securement device is more rigid, the channel may be smaller than the catheter diameter, but closer to the same size as the catheter (e.g., less than 10%, 5%, or 2% smaller).

Channel 304 may also have a surface friction pattern that grips the catheter and/or otherwise reduces pistoning of the catheter within the securement device. The friction pattern may be serrations, bumps, protrusions, scaling (e.g., shark scale pattern) on the surface of the securement device where the catheter is in contact during use (e.g., within the channel). The friction pattern may be molded into the body of the securement device or may be applied to the surface of the securement device material after molding.

In addition to surface features, the length of the channel in contact with the catheter and the extent to which the catheter securement device encircles the catheter may determine in part the difficulty with which the catheter can be moved within the channel (i.e., the tendency for pistoning). In some embodiments, the length of the channel may be greater than or equal to 0.5, 0.75, 1.0, 1.25, 1.5, or 2 inches and/or less than or equal to 3, 2.5, 2, or 1.75 inches or within a range thereof.

The securement device preferably has a low profile. In some embodiments, the height (i.e., standoff from the surface of the skin of a patient) is greater than 0.1, 0.15, 0.2, 0.25, and/or less than 0.8, 0.6, 0.4, or 0.35 inches or within a range thereof.

In some embodiments bottom surface 322 may have an adhesive pad to adhere the securement device to the skin. The adhesive may be used with or without eyelets and/or stitching. In some embodiments body 302 may be rigid and the pad applied to bottom surface 302 may provide sufficient padding to avoid harming the skin of the patient.

Securement device 300 may include an antimicrobial agent coated on a surface thereof or impregnated into the material. For example, the material of channel 304 may include an antimicrobial agent. Alternatively, cover 340 may include an antimicrobial agent. The antimicrobial agent may be applied to the underside such that the antimicrobial agent comes into direct contact with the catheter and/or channel. Placing the antimicrobial agent on the cover 340 can simplify the process for reapplying the antimicrobial agent after the securement device has been applied for a period of time. Instead of replacing the entire device and risking disturbing the catheter, the cover can be replaced to reapply the antimicrobial agent or to allow temporary access to the catheter for cleaning or inspection. Any antimicrobial known in the art can be used, including, but not limited to chlorhexidine.

The securement device can be particularly advantageous when used for placing catheters into the internal jugular vein. Internal jugular catheters are susceptible to infection from ports positioned near the neck and hair. By turning the catheter to face down, the ports lie close to the chest where they are less likely to be tangled and/or contaminated. Figure illustrates a triple lumen central line catheter 400 placed into the skin of patient and inserted into the jugular vein with the tip of the catheter positioned near the heart (e.g., in the superior vena cava). Catheter 400 includes 3 ports 402a, 402b, and 402c. Catheter 400 is secured to the skin of the patent using securement device 300 having a body 302 that is sutured to the patient and a cover 340 that locks the catheter into body 302. In one embodiment, a method includes placing central venous catheter 400 in the internal jugular vein of the patient. The catheter is then placed in a channel of body 302, which redirects the catheter downward. A cap 340 is applied to body 302. Sutures are then placed in body 302 and the skin of the patient to secure device 300 to the skin of the patient.

The present invention includes kits. The kits can include any of the catheter securement devices described herein and a procedure tray, a catheter, and an apparatus for inserting the catheter into a body lumen (e.g., a vein) or a body cavity (e.g., an abdominal cavity) of a patient.

The kit may also include one or more of an anesthetic, a sterilizer for the patient's skin, a needle and suture or staples, a guide wire, a hollow or 'cook' needle for central venous puncture, a dilator, and a scalpel. Apparatus for inserting the catheter may further include a suture needle and a length of suture, a surgical stapler, an adhesive, and/or one or more other suitable mechanisms for affixing the catheter securement device to the patient's skin.

The methods of the present invention can be performed using any of the catheter securement device described herein. The method includes causing a bent profile in the catheter using the securement device to position the catheter at a desired angle and location. The methods described in Applicant's provisional applications 61/902,224 and 62/001,629, and PCT/US2012/036963 illustrate catheters and methods that can be applied to the securement devices described herein. The devices described herein may be used with any of the features described in 61/902,224; 62/001,629; and/or PCT/US2012/036963.

Some embodiments of the invention relate to securement device used for placement of a peripheral inserted central catheter (PICC). When used with a PICC, the securement device is used to turn the catheter up the arm, which results in less kinking and reduced pistoning of the catheter.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A catheter clamp for use in securing a catheter in a vein of a patient, the catheter clamp comprising:

a catheter clamp body defining a curved channel extending between a first end and a second end thereof, the curved channel having an opening and a diameter configured to accommodate a tubing of the catheter, the catheter clamp body has a surface for contracting the skin of a patient, the clamp body being shaped to orient a free end of the tubing away from a direction of catheter insertion and to support a bent profile of the tubing, thereby reducing the risk of kinking the tubing, the clamp body further defining an elongate opening which communicates the channel along a length thereof with the environment, the elongate opening having a width which is dimensionally smaller than the diameter of the channel, a securement structure coupled to the catheter clamp body for affixing the catheter clamp to the skin of the patient; and a cover, displaceably positioned on the catheter clamp body for restricting access to the elongate opening, the cover being configured to slide along a surface of the clamp body to form a releasable cover over the elongate opening for securing the catheter in the channel.

2. The catheter clamp of claim 1, wherein the elongate opening provides a passageway from the environment through the clamp body into the channel.

3. The catheter clamp of claim 1, wherein the elongate opening is configured to extend from the first end to the second end of the curved channel.

4. The catheter clamp of claim 1, wherein the clamp body is constructed of a flexible material.

5. The catheter clamp of claim 4 wherein the flexible material of the clamp body is sufficiently elastic to return the width of the elongate opening to an original configuration thereof, existing prior to the application of a force to the clamp body, once the force causing the flexure is no longer being applied to the catheter clamp body.

6. The catheter clamp of claim 1 wherein the catheter clamp is constructed of a flexible material having a Shore hardness less than 85 D.

7. The catheter clamp of claim 1, wherein the clamp body is constructed of a flexible material which permits the clamp body to flex upon the application of a force thereto, wherein a flexure of the clamp body functions to increase the width of the elongate the opening sufficient to permit the passage therethrough of the tubing of the catheter and the lodging of the tubing within the clamp body channel.

8. The catheter clamp of claim 1 further including the cover, displaceably positioned over the clamp body, for restricting access to the elongate opening.

9. The clamp body of claim 1 wherein the clamp body includes the structure positioned along a length of the channel for resisting a displacement along the length of the channel of the catheter tubing positioned within the channel.

10. A method for securing a catheter to a patient's skin, the method comprising:

a positioning the catheter as in claim 1 in the superior vena cava of a patient;

a positioning a free end of the catheter in the catheter clamp of claim 1; and securing the catheter clamp to the patient's skin.

11. The method of claim 10, wherein the catheter clamp is secured to the patient's skin with at least one suture or staple passing through at least one eyelet of the clamp and into the patient's skin.

12. The method of claim 10, wherein the catheter and the catheter clamp are secured at the a jugular position.

13. The method of claim 10, wherein the size of the catheter is in a range from 5 French to 7 French and wherein the curve of the curved body of the clamp prevents kinking of the catheter in the channel.

* * * * *